United States Patent [19]

Kawahara et al.

[11] 4,431,421

[45] Feb. 14, 1984

[54] DENTAL RESTORATIVE COMPOSITION

[75] Inventors: Haruyuki Kawahara, Moriguchi; Teruo Makita, Kobe; Shozo Kudo, Minoo; Takashi Funakoshi, Osaka, all of Japan

[73] Assignee: Kanebo, Ltd., Tokyo, Japan

[21] Appl. No.: 315,811

[22] Filed: Oct. 28, 1981

[51] Int. Cl.$^3$ .............................................. A61K 6/08
[52] U.S. Cl. ..................................... 433/228; 106/35; 260/998.11; 433/199; 433/201; 433/202; 433/212; 433/217; 433/222; 523/115; 523/116; 523/117; 523/118
[58] Field of Search .................. 260/998.11; 430/288; 523/115, 116, 117, 118; 433/199, 201, 202, 217, 228; 106/35; 524/780

[56] References Cited

U.S. PATENT DOCUMENTS

| | | | |
|---|---|---|---|
| 3,066,112 | 11/1962 | Bowen | 260/41 |
| 3,261,686 | 7/1966 | Celeste et al. | 430/288 |
| 3,539,533 | 10/1970 | Lee et al. | 260/47 |
| 3,835,090 | 9/1974 | Gander et al. | 260/42.15 |
| 3,926,906 | 12/1975 | Lee et al. | 106/35 |
| 4,200,723 | 4/1980 | Chen | 528/1 |
| 4,293,636 | 10/1981 | Okuya | 430/281 |
| 4,298,679 | 11/1981 | Shinozaki et al. | 430/288 |
| 4,327,014 | 4/1982 | Kawahara et al. | 523/116 |

*Primary Examiner*—Lorenzo B. Hayes
*Attorney, Agent, or Firm*—Flynn, Thiel, Boutell & Tanis

[57] ABSTRACT

Resin-forming dental restorative material comprising a blend of dipentaerythritol penta- and hexa-acrylate or -methacrylate optionally, tetramethylolmethane tri- or tetra-acrylate or tetramethylolmethane tri- or tetra-methacrylate and a filler having a Mohrs' hardness of at least 5.

10 Claims, No Drawings

DENTAL RESTORATIVE COMPOSITION

The present invention relates to a restorative material for medical or dental use consisting predominantly of a resin-forming material for medical or dental use and a restorative implant material, and more particularly, to a restorative material for medical or dental use applicable in the field of repairing bones and teeth which is extremely excellent in physical properties, such as hardness, compressive strength, abrasion resistance and so on, as well as in bonding to the hard tissue of the human body.

Explanation will be given hereinafter of the restorative material for medical or dental use of the present invention. Of the medical or dental restorative materials, particularly of the dental restorative materials, the dental amalgam consisting of silver alloy and mercury, and silicate cement have hitherto been used as restorative filling materials. The amalgam, however, shows a low degree of seal to the margins of a tooth cavity because of its inferior impact strength in addition to its inferior bonding property to teeth, and also there is the fear that it will exert an unfavourable influence on the human body because of toxicity. Further, the silicate cement is readily soluble and entails such shortcomings as pulpal irritation, in addition to a low degree of bonding property to teeth and inferior marginal seal.

Whereupon, for anterior teeth, developments have been made of a material consisting predominantly of bisphenol A diglycidyl methacrylate (hereinafter called "Bis-GMA" for short) and an inorganic filler, such as α-quartz (hereinafter called the Bis-GMA type composite resin), as a new restorative filling material useful as a substitute for conventional silicate cement (refer, for instance, to the U.S. Pat. Nos. 3,539,533; 3,066,112; 3,926,906, etc.

This material has improved properties such as compressive strength, water resistance, pulpal irritation and so on as compared to conventional materials, such as said silicate cement, and it is widely used. But that material is still far from satisfactory in the aspects of physical properties, such as hardness, compressive strength, abrasion resistance and so on, or bonding to teeth and the like. In the case of Bis-GMA, it is not completely satisfactory even for anterior teeth, not to mention that it is next to impossible to apply it to molars which are subjected to higher occlusal pressures than anterior teeth.

With the Bis-GMA type composite resin, as the reason why said physical functions are not sufficient it can be said that Bis-GMA is insufficient in physical properties as a resin, because it is low in cross-linking and it has a high viscosity. Even if diluents were jointly used therewith, the amount of the inorganic filler which is jointly used for the purpose of improving the physical properties of restorative filling material is restricted.

In order to improve the various shortcomings of the Bis-GMA type composite resin, attempts were made to increase the cross-linking of the resin and increase the amount of inorganic filler used therewith by using such low viscosity multifunctional monomers as trimethylolpropane trimethacrylate (hereinafter called "TMPT" for short) instead of Bis-GMA as disclosed in the U.S. Pat. No. 3,835,090, for instance. But in the case of TMPT, bonding to teeth is hardly shown because it has no polar groups and the viscosity of TMPT is too low, which gives rise to such problems as a lack in the surface curability of the composite resin and setting of the inorganic filler in a paste condition.

The instant inventors studied for the purpose of solving said various drawbacks of conventional dental materials, in consequence of which it was found that by using a resin-forming material consisting predominantly of the hereinafter-described acrylic monomer of the specified structure, there could be obtained a material for medical or dental use which is excellent in various physical properties, such as hardness, compressive strength, abrasion resistance and so on, weak in tissue irritation and in addition, excellent in bonding to the hard tissue of the human body.

The present invention is designed to provide a resin-forming material suitable for medical or dental use which is excellent in various physical properties, such as hardness, compressive strength, abrasion resistance and so on, weak in the tissue irritation and added to this, extremely good in the bonding to the hard tissue of the human body.

Another purpose of the present invention is to provide resin-forming material suitable for medical or dental use which is excellent in various physical properties, tissue irritation and bonding to the hard tissue and good in operation in its practical use.

The other purposes and merits of the said resin-forming material of the present invention will be clear from the explanations which follow.

According to the present invention, the said purposes and merits could be achieved by a resin-forming material suitable for medical or dental use comprising at least one compound having the formula (I):

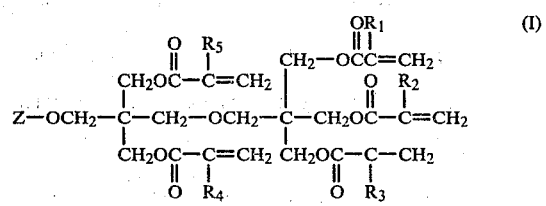

wherein Z is hydrogen or

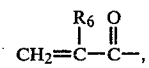

and $R_1$, $R_2$, $R_3$, $R_4$, $R_5$ and $R_6$, which are the same or different, each is selected from the group consisting of hydrogen, methyl or ethyl.

Compounds represented by the said formula (I) divide broadly into two classes, one is compounds represented by the following formula (II) and the other is compounds having the formula (III). Formula (II):

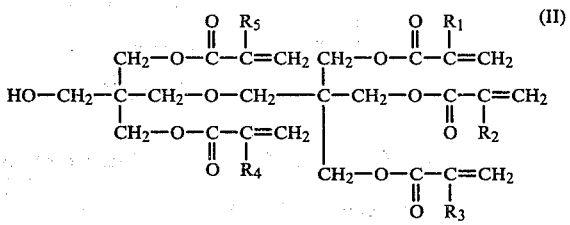

wherein $R_1$, $R_2$, $R_3$, $R_4$ and $R_5$ have the same meanings as defined in the formula (I).

Formula (III):

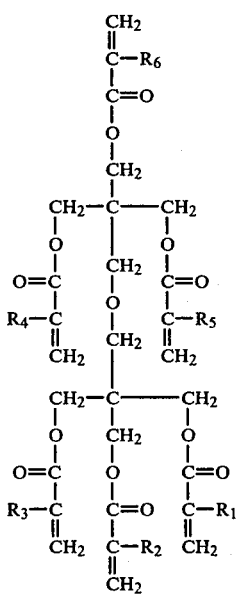

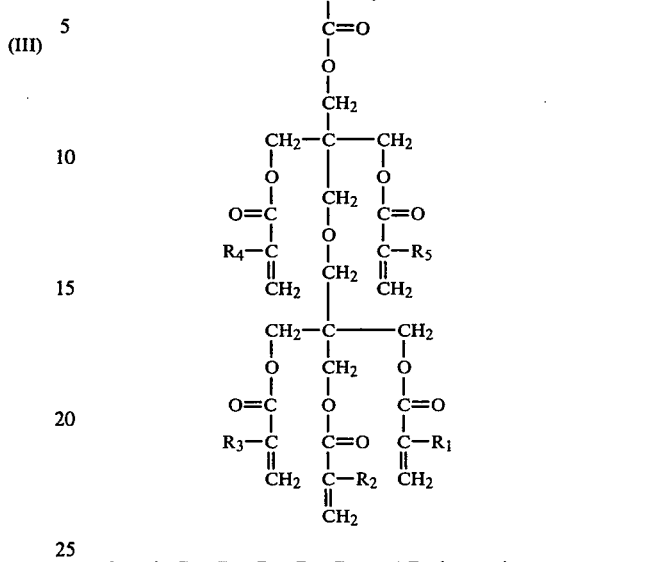

wherein $R_1$, $R_2$, $R_3$, $R_4$, $R_5$ and $R_6$ have the same meanings as defined in the formula (I).

According to the present invention at least one compound represented by the formula (II) or (III) can be used as a resin-forming material suitable for medical or dental use.

In the present invention it is preferred to use, as the medical or dental resin-forming material, compositions comprising (1) 30–100% by weight of at least one compound having the following formula (II):

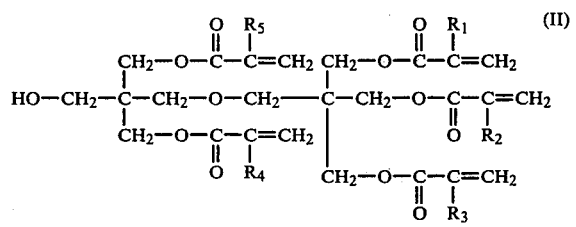

wherein $R_1$, $R_2$, $R_3$, $R_4$ and $R_5$ have the same meanings as defined in the formula (I) and (2) 0–70% by weight of at least one compound having the following formula (III):

wherein $R_1$, $R_2$, $R_3$, $R_4$, $R_5$ and $R_6$ have the same meanings as defined in the formula (I).

With the resin-forming material of the present invention the compound represented by the formula (II) should advantageously be mixed in proportions of preferably 30–95% by weight, more preferably 40–80% by weight and most preferably 45–70% by weight and the compound represented by the formula (III) in proportions of preferably 5–70% by weight, more preferably 20–60% by weight and most preferably 30–55% by weight. If the compound represented by the formula (II) is less than 30% by weight, viz., the compound represented by the formula (III) is in excess of 70% by weight, in the case, in particular, of using same as a dental filling material or restorative for a crown bridge, it tends to deteriorate in the bonding to teeth and operation.

In the instant invention, the said formulae (I), (II) and (III) wherein $R_1$, $R_2$, $R_3$, $R_4$, $R_5$ and $R_6$ are hydrogen or methyl, in particular, are preferred. In this case, most typically the respective $R_1$, $R_2$ and $R_3$ in the formula (II) or the respective $R_1$, $R_2$, $R_3$, $R_4$, $R_5$ and $R_6$ in the formula (III) represent hydrogen or methyl. Not only that, but also those in which part of $R_1$, $R_2$, $R_3$, $R_4$, $R_5$ and $R_6$ represents hydrogen, whereas another part of them represents methyl, viz., mixed esters of acrylic acid and methacrylic acid, are also preferred.

As typical examples of compounds represented by the formula (II) there are cited dipentaerythritol pentacrylate (DPE-5A) an dipentaerythritol pentamethacrylate (DPE-5M), for instance. As typical examples of compounds represented by the formula (III) there are cited dipentaerythritol hexacrylate (DPE-6A) and dipentaerythritol hexamethacrylate (DPE-6M), for instance.

Conventionally, as already mentioned, it is known to use triacrylate or trimethacrylate esters of trimethylolpropane, but the compound of the said formula (II) used in the present invention is characterized by possessing another methylol group (—CH$_2$OH), compared to those pentacrylate or pentamethacrylate esters, and the compound of the said formula (III) is characterized in that it is a hexafunctional acrylate or methacrylate ester.

The compound of the said formula (II) is excellent in bonding to the hard tissue of the human body caused by the effect of the four methylol groups and by using such compound of the formula (II) and compound of the formula (III) in combination. In particular, a resin for medical or dental use can be advantageously formed which is excellent in bonding to the hard tissue of the human body as well as in the compressive strength.

In the case, further, of using a combination of the compound of formula (II) and the compound of formula (III), the composite resin formed therefrom is excellent in water resistance and slight in tissue irritation besides the aforementioned characteristics and show very excellent operation on the occasion of its practical use.

On top of that, the compounds of the present invention represented by the formulae (II) and (III) can be used in combination with other polymerizable monomers, such as conventionally known resin-forming monomers for medical or dental use. In this case, the amount in which the other monomers are incorporated is 0–90% by weight, more preferably 60% by weight or less and most preferably 20% by weight or less. Other monomers, however, may be present in the amount of 60–90% by weight on the occasion that the compounds of the formulas (II) and (III) are used for the purpose of reinforcing physical properties of cured products or of improving operation as a reactive dilutent or viscosity controller for other monomers. In this connection, as typical examples of the polymerizable monomers referred to here, there can be cited not only the known monomers, such as bismethacryloxyethoxydiphenylpropane, bis-GMA, bisphenol-A dimethacrylate, neopentylglycol dimethacrylate, diethyleneglycol dimethacrylate, triethyleneglycol dimethacrylate, 2-hydroxyethyl methacrylate and so on but also the compounds which are represented by the following formula (IV):

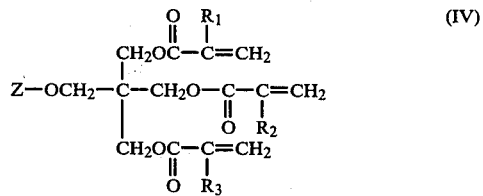

wherein Z is hydrogen or

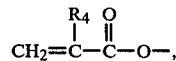

and $R_1$, $R_2$, $R_3$ and $R_4$, which are the same or different, each is selected from the group consisting of hydrogen, methyl, or ethyl,
said compound belonging to Japanese Patent Application No. 55-41,084, U.S. patent application Ser. No. 138,814 and European Patent Application No. 80101964.7, discovered by the instant inventors.

The tetramethylolmethane tri- or tetra-acrylate or -methacrylate represented by the above formula IV, as mentioned in the said U.S. patent application Ser. No. 138,814 and European Patent Application No. 80101964.7 specifications, is very superior as the dental resin-forming monomer. The monomer of the formula IV, however, is, in itself, generally low in viscosity, entailing such drawbacks as to cause the setting of a part of the filler when preserved in admixture with inorganic fillers.

On the other hand, a blend of 60–90% by weight of the monomer of the formula IV and 40–10% by weight of the monomer (dipentaerythritol penta- or hexa-acrylate or -methacrylate) having the aforesaid formula I of the present invention, as the hereinafter-described Table 7 shows, does not cause the setting of the filler even if preserved, with its much better operation, due to its adequate viscosity and a very excellent dental resin-forming material is formed from this blended monomer composition.

In the case of using the monomer of the formula I of the present invention in combination with the monomer of the said formula IV in this manner, it is particularly preferred to use a mixture of 45–70% by weight of the monomer of the formula II and 55–30% by weight of the monomer of the formula III. If such mixture of monomers of the formula II and of the formula III is used in admixture with the monomer of the formula IV, besides the aforesaid advantages, there can be gained such advantage that when it is cured, the uncured percentage of the monomer concerned in the surface portion where such cured product comes in contact with air is reduced to a much lower value.

The resin-forming material of the present invention, in its practical use, should usually be used as a composition in admixture with a catalyst for causing the polymerization of the compound of the formula (II) and/or compound of the formula (III) and an activator for accelerating the formation of free radicals by the reaction with such a catalyst.

Furthermore, the compounds of the formula (II) and/or formula (III) can be used in combination with any inorganic fillers for medical or dental use which are non-toxic to the human body and have a great hardness, such as powdered quartz, powdered glass, glass beads, powdered aluminum oxide, borosilicate glass, barium glass, hydroxy apatite and alumino silicate, in addition to the catalyst and activator. These inorganic fillers, although it differs according to use, should preferably have a Mohs' scale of hardness of at least 5 and, preferably, at least 6. In this case, however, the physical properties, as a material for medical or dental use, are much better if the resin-forming material is used in combination with metal nitride. The said inorganic filler should preferably account for 30–95% by weight, more preferably 50–90% by weight, and most preferably 70–90% by weight, based on the total amount of the composition of the filler and the resin-forming compound (monomer) such as compound of the formula (II) or (III).

If the inorganic filler is pretreated with a keying agent, such as γ-methacryloxypropyltrimethoxysilane, vinyltriethoxysilane and so forth, the bond between the formed resin and the inorganic filler will be intensified and the physical properties as a material for medical or dental use will be further improved.

The monomer of the present invention represented by the said formula (II) or (III) is readily polymerized and cured by means of a catalyst. On this occasion, the application of heat often does harm to the human body and it is preferred to divide the said monomer, into two, liquid portions, one containing a catalyst and the other containing an activator, in such a manner that the monomer can be cured at normal temperature by mixing both liquids immediately prior to use.

As the catalyst, peroxide is preferred and it should preferably be used in combination with the activator. As the peroxide catalyst, there can be cited, for instance, diacyl peroxides, such as benzoyl peroxide, parachlorobenzoyl peroxide, 2,4-dichlorobenzoyl peroxide, acetyl peroxide, lauroyl peroxide and so on, hydroperoxides, such as tertiary butyl hydroperoxide, cumene hydroperoxide, 2,5-dimethylhexane-2,5-dihydroperoxide and so on, ketone peroxides, such as methyl ethyl ketone peroxide and so on, peroxycarbonates, such as tertiary butyl peroxybenzoate and so on, etc.

These peroxide catalysts should preferably be used in proportions of 0.1–2.5% by weight based on the total weight of the polymerizable monomers of the present invention represented by the said formula (II) or (III).

As the activator capable of use in combination with the peroxide, there can be cited, for instance, tertiary amines, such as N,N-bis-(2-hydroxyethyl)-4-methylaniline, N,N-bis-(2-hydroxyethyl)-3,4-dimethylaniline, N,N-bis-(2-hydroxyethyl)-3,5-dimethylaniline, N-methyl-N-(2-hydroxyethyl)-4-methylaniline, 4-methylaniline, N,N-dimethyl-p-toluidine, N,N-dimethylaniline, triethanolamine and so on, and in addition, transition metal ions, such as cobalt naphthenate, cobalt octanate and so on, amine salts of p-toluenesulphonic acids and sulphinic acids and so forth.

These activators can generally be used in proportions of 0.1 to 2.5% by weight based on the total weight of the said polymerizable monomers.

The monomer of the present invention can also be polymerized and cured by irradiation of ultraviolet rays. In this case, it is not necessary to formulate the composition into the said two-liquid form and it is preferred to use a photosensitizer in the amount of 0.1–10% by weight based on the total weight of the polymerizable monomers. As the photosensitizer, there can be cited, for instance, carbonyl compounds, such as benzoin, benzoin methyl ether, benzoin ethyl ether, acetoin benzophenone, p-chlorobenzophenone, p-methoxybenzophenone and so on, sulphur compounds, such as tetramethylthiuranium monosulphide, tetramethylthiuranium disulphide and so on, azo compounds, such as azobisisobutyronitrile, azobis-2,4-dimethylvaleronitrile and so on, peroxide compounds, such as benzoyl peroxide, tertiary butyl peroxide and so on, etc.

For the enhancement of the preservability of the resin composition, it is effective to add an UV absorber such as benzophenone type compound, such as 2-hydroxy-4-methylbenzophenone, in an amount of 0.5–2.0 parts by weight, based on 100 parts by weight of the resin composition, or a stabilizer generally called a free radical inhibitor, such as p-methoxyphenol, 2,5-ditert.-butyl-4-methylphenol and so on, in an amount of 0.05–0.20 part by weight, based on 100 parts by weight of the resin composition.

For a method of using such resin compositions, it is very convenient to prepare in advance a first paste-like substance (paste A) comprising an inorganic filler, resin composition and activator and a second paste-like substance (paste B) comprising an inorganic filler, resin composition and catalyst, for instance, since the polymerization is initiated upon mixing these two pastes when used by doctors.

In the case of using such material in the restoration of the hard tissue of the human body, such as teeth and bones, the said material possesses sufficient bonding to the hard tissue, but it is also effective to apply the said material after precoating the hard tissue with a bonding agent in ordinary use, such as 2-hydroxy ethylmethacrylate and so on, for the purpose of improving the bonding to the hard tissue. As the said bonding agent, the subject matter of another co-pending Patent Application filed claiming the priorities based on Japanese Patent Application No. 54-44751, U.S. Pat. No. 138,814 and European Patent No. 80101965.4 discovered by the instant inventors, can be very effectively used, which bonding agent consists predominantly of a composition comprising 50–99.5% by weight of polymerizable acrylate esters and/or methacrylate esters having hydrophilic groups comprising carboxyl, epoxy, amino or hydroxyl, and 0.5–50% by weight of at least one member of organic metal compounds selected from the group consisting of alkoxy-containing titanium compounds and silicon compounds.

Thus, according to the present invention there can be obtained resin compositions suitable for medical or dental use which are extremely excellent in various physical properties after curing, such as hardness, compressive strength, abrasion resistance, weak in tissue irritation and good in bonding to the hard tissue of the human body and on top of that, excellent in operation in practical use.

Further, the resin-forming material of the present invention can be advantageously used, in medical or dental use, not only as a material for bone cement and artificial bones in the orthopedic surgery and restorative surgery field, but also as a restorative material for crown bridges, core material for crowns, dental cement, filling material, cavity lining material, root canal filling material and so on, in the operative dentistry and prosthetic dentistry field in particular.

The present invention will be specifically explained with the reference to working examples as follows. Unless otherwise specified, "part" and "%" in the examples mean "part by weight" and "% by weight". Further, in the examples the composition of the resin-forming material (monomer) and filler prior to curing treatment is called the "composite resin" for short for convenience's sake.

In this connection, in the examples the method for the preparation of the composite resin and methods for the measurement of compressive strength, abrasion, water sorption, hardness, toothbrush abrasion, coloring, linear thermal expansion coefficient, and tensile strength follow the hereinafter-described procedures.

(1) A method for the preparation of composite resin:
(1)-1. Preparation of filler:

100 gr. of powdery filler classified to a particle size of 50 microns or less was mixed in an aqueous solution obtained by vigorously mixing 10 g of γ-methacryloxypropyltrimethoxysilane and 1 ml of acetic acid with agitation by addition of 200 ml of water and the powdery filler was separated after agitation. Powdery filler so separated was dried in a hot air dryer held at 105° C. for 24 hours whereby a silane-treated filler was prepared.

In the Examples, the fillers were all treated with silane and then used.

(1)-2. Preparation of monomer paste:

Monomer was divided into two equal parts, one monomer was incorporated with a polymerization activator and the filler prepared by the procedure of (1)-1 above (hereinafter called Paste A for short) and the other monomer was incorporated with a catalyst and a filler prepared by the procedure of (1)-1 (hereinafter called Paste B for short).

In the Examples, N,N-bis-(2-hydroxyethyl)-4-methylaniline as used as the activator and benzoyl peroxide was used as the catalyst.

For the amount in which the activator was mixed to Paste A and the amount in which the catalyst was mixed to Paste B, they were formulated in such a manner that curing should occur about 3 minutes after mixing Paste A and Paste B.

(1)-3. Preparation of composite resin:

Paste A and Paste B were taken each in equal amounts, mixed and kneaded together on a kneading paper at room temperature for 30 seconds whereby a composite resin was prepared.

(2) Measurement of compressive strength:

Based on Americal Dental Association (ADA) Specification No. 9 for Dental Silicate Cement, compressive strength was measured by the following procedures.

Composite resin was loaded in a mould, sealed with sheeted glass, then placed in a pressure vessel and left to stand under an atmosphere of 37° C. and relative humidity of 100% for 15 minutes. The cured composite resin was taken out from the mould and immersed in water held at 37° C. for 24 hours whereby specimens were prepared. By using an Instron tester, the specimens were pressed at conditions of press rate of 0.2 mm/min. to determine their compressive strength.

(3) Measurement of abrasion loss:

Cured composite resin loaded in and taken out from the mould by following the procedures set forth in section of "(2) Measurement of compressive strength" was used as specimens for measurement of abrasion loss. The specimens were dried in a hot air dryer held at 100° C. for 24 hours and then cooled in a desiccator for one hour and weighed. The specimens were placed in a cylindrical metal ball mill with an inner capacity of 500 ml and inner diameter of 10 cm and simultaneously, 20 stainless steel balls of 1 mm diameter and 200 ml of polishing paste prepared by adding 900 parts by weight of distilled water to 200 parts by weight of powdered $Si_3N_4$ passing through a 325 mesh sieve, as a polishing material, were loaded the ball mill was, sealed and then rotated at a rate of 100 r.p.m. for 78 hours. After it was finished, the specimens were washed with water, dried in the hot air dryer held at 100° C. for 24 hours and cooled in the desiccator for another one hour and weighed. Abrasion loss was calculated according to the following equation:

Abrasion loss ($cm^3$) = [(weight of unpolished specimens) − (weight of polished specimens)]/(density of specimens)

(4) Measurement of amount of water sorption:

Based on American Dental Association (ADA) Specification No. 27 for Direct Filling Resins, the amount of water absorbed was measured by the following procedure.

Composite resin was cured to prepare a disk specimen 20 mm across and 1 mm thick. The specimen was left to stand in a constant temperature dryer held at 37° C., then placed in the desiccator, cooled for one hour and weighed. Value when a constant quantity was reacted with repetition of this operation was set as dry weight. Then, the specimen was immersed in water held at 37° C. for 7 days, then taken out, the water on the surface was wiped off with soft gauze and the specimen was weighed to determine the weight of water absorbed. The amount of water absorbed was calculated by the following equation:

Amount of water sorption ($mg/cm^2$) = [(weight after immersion) − (dry weight)]/surface area of specimen (5) Measurement of hardness:

Measurement was made of Knoop hardness by means of a microhardness tester of Shimazu make. Composite resin was cured to prepare a columnar specimen 10 mm across and 5 mm high and a load of 900 g was applied on the flat surface of the specimen for 15 minutes. The length of the dent formed on the surface of the specimen was measured to determine the Knoop hardness.

(6) Toothbrush abrasion test:

Composite resin was cured to prepare and fix a columnar specimen 13 mm across and 4 mm high. A commercially available toothbrush with a load of 200 g was applied to the flat portion of the specimen and this toothbrush was reciprocated at a stroke of 2 reciprocations/second to polish the specimen surface. In the meantime, a solution prepared by diluting 150 g of commercially available toothpaste to ½ with water was continuously added dropwise. After 8 hours the specimen was washed with water, dried and weighed. Rate of toothbrush abrasion loss was calculated by the following equation.

$$\text{Rate of toothbrush abrasion loss (\%)} = \frac{\text{(weight of specimen before abrasion)} - \text{(weight of specimen after abrasion)}}{\text{(weight of specimen before abrasion)}} \times 100$$

(7) Coloring test:

Disked test pieces 13 mm across and 4 mm high were surface-polished with No. 800 emery paper and then immersed in commercially available aqueous coffee solution (solution obtained by dissolving 2.5 g of powdered coffee in 100 ml of water) at 37° C. for 4 days. The specimens were washed with water, dried and then their color was measured by means of a colorimeter, a product of Nippon Denshoku Kogyo Company, to read the values L, a and b. Likewise, the values $L_0$, $a_0$ and $b_0$, which were the measured color values of the specimen surfaces prior to immersing into the coffee solution, were read, the degree of discoloration $\Delta E$ was calculated by the following equation and $\Delta E$ was set as a basis for coloring. The greater is the value of $\Delta E$, the greater is the degree of discoloration. This test was also effected on the surface of the unpolished specimen.

$$\Delta E = \sqrt{(L - L_0)^2 + (a - a_0)^2 + (b - b_0)^2}$$

(8) Measurement of linear thermal expansion coefficient:

Composite resin was enclosed in a glass tube 5 mm in diameter and 20 mm in length, the opening of the tube was sealed with a cover glass for microscope, left to stand at room temperature for 15 minutes and then the cured composite resin was taken out from the glass tube whereby specimens for measurement were prepared.

Measurement was made of the linear thermal expansion coefficient of the specimens so prepared by means of linear thermal expansion measuring instrument, a product of Rigaku Denki Company. In making the measurements, the heating and temperature raising rate was set at 5° C./min.

(9) Measurement of tensile strength:

Based on pressure tear test according to ADA Specification No. 27 for the diametrial method, the tensile strength was measured by the following procedure.

Composite resin was loaded in a stainless steel mould 6 mm in inner diameter and 3 mm in height and the opening of the mould was sealed with a cover glass for a microscope. The mould was left to stand under an atmosphere of 37° C. and relative humidity of 95% for 15 minutes. After that, the cured composite resin was taken out from the mould. This cured composite resin was polished by use of powdered SiC and then immersed in the water held at 37° C. for 24 hours whereby specimens for measurement were prepared.

Tensile strength of the specimens so prepared was measured by means of an Instron tension tester. In making the measurements, the head press rate was set at 1 cm/min.

(10) Bonding strength:

(1) Bonding strength to bovine dentin:

A fresh anterior bovine tooth implanted into a square rod made of acryl resin was polished with emery paper until the dentin was exposed, and further polished and finished with No. 800 emery paper for the formation of a contact surface whereby there was prepared a testpiece of material for the bonding test with the bovine dentin. This bonding testpiece was stored in water. It was taken out from the water immediately before the measurement was made. The surface of the testpiece was well wiped off and further dried in a weak air stream. Then, the bonding surface of the bovine dentin was coated with composite resin and the square rod made of acryl resin was stuck and pressed against the coated surface. It was left to stand at room temperature for 15 minutes and then immersed in water held at 37° C. for 24 hours. Both ends of the acryl resin square rods of the specimen were pulled apart at a rate of 1 mm/min. to determine the bonding strength. The bonding strength was indicated by the maximum value and the minimum value of measured numericals when measuring the respective specimens for every 20 testpieces.

(2) Bonding strength to bovine enamel:

A fresh anterior bovine tooth implanted in a square rod made of acryl resin was polished and leveled with emery paper, and further polished and finished with No. 800 emery paper for the formation of a bonding surface whereby there was prepared a testpiece of material for the bonding test with the bovine enamel. This bonding testpiece was stored in water. It was taken out from the water immediately before the measurement was made. The surface of the testpiece was well wiped off and etched with 50% aqueous phosphate solution for one minute. It was successively washed with water and air dried using a weak air stream. Using the testpiece of material for the bonding test with the bovine enamel so prepared, its bonding strength was measured following the same procedure as in the case of the measurement of the bonding strength with the bovine dentin and the measured values were indicated in the same manner.

EXAMPLE 1

Silane-treated $\alpha$-SiO$_2$ was prepared following the procedure for the preparation of filler in section (1)-1. Then, using mixed monomers, as the monomer component, prepared by mixing dipentaerythritol pentacrylate (DPE-5A) and dipentaerythritol hexacrylate (DPE-6A) in proportions of 55:45 (by weight ratio), silane-treated $\alpha$-SiO$_2$, catalyst and activator, the mixed monomer was divided into two equal parts for the preparation of Paste A1-1 and Paste B1-1 of the following compositions according to the procedure for the preparation of monomer paste in section (1)-2.

Paste A1-1 and Paste B1-1 so prepared were taken each in equal amounts, mixed and kneaded together on kneading paper at room temperature for 30 seconds whereby a composite resin was prepared.

This composite resin was loaded in a stainless steel pipe with inner diameter of 10 mm and height of 5 mm at one end and the excess part was removed off with sheeted glass. An injection needle was stuck into the surface of the composite resin at intervals of 10 seconds at room temperature to measure the curing time. It was about 3 minutes long.

|  | Part by weight |
|---|---|
| Paste A1-1 |  |
| Dipentaerythritol pentacrylate (DPE-5A) | 55 |
| Dipentaerythritol hexacrylate (DPE-6A) | 45 |
| Silane treated $\alpha$-SiO$_2$ | 300 |
| N,N—bis-(2-hydroxyethyl)-4-methylaniline | 0.8 |
| Paste B1-1 |  |
| Dipentaerythritol pentacrylate (DPE-5A) | 55 |
| Dipentaerythritol hexacrylate (DPE-6A) | 45 |
| Silane treated $\alpha$-SiO$_2$ | 300 |
| Benzoyl peroxide | 0.8 |

Compressive strength, abrasion loss and bonding strength were measured of the composite resin and results were shown in Table 1.

Paste A's and Paste B's of following compositions were formulated using various monomers conventionally known as resin-forming material for medical or dental use instead of the mixed monomer of DPE-5A and DPE-6A.

|  | Part by weight |
|---|---|
| Paste A1-2 |  |
| Bisphenol A diglycidyl methacrylate (Bis-GMA) | 80 |
| Triethyleneglycol dimethacrylate (TEGDMA) | 20 |
| Silane treated $\alpha$-SiO$_2$ | 300 |
| N,N—bis(2-hydroxyethyl)-4-methylaniline | 0.8 |
| Paste B1-2 |  |
| Bisphenol A diglycidyl methacrylate (Bis-GMA) | 80 |
| Triethyleneglycol dimethacrylate (TEGDMA) | 20 |
| Silane treated $\alpha$-SiO$_2$ | 300 |
| Benzoyl peroxide | 0.8 |
| Paste A1-3 |  |
| Bismethacryloxyethoxydiphenylpropane (Bis-MEPP) | 80 |
| Triethyleneglycol dimethacrylate (TEGDMA) | 20 |
| Silane treated $\alpha$-SiO$_2$ | 300 |
| N,N—bis(2-hydroxyethyl)-4-methylaniline | 1.0 |
| Paste B1-3 |  |
| Bismethacryloxyethoxydiphenylpropane (Bis-MEPP) | 80 |
| Triethyleneglycol dimethacrylate (TEGDMA) | 20 |
| Silane treated $\alpha$-SiO$_2$ | 300 |
| Benzoyl peroxide | 1.0 |
| Paste A1-4 |  |
| Neopentylglycol dimethacrylate (NPGDMA) | 100 |
| Silane treated $\alpha$-SiO$_2$ | 300 |
| N,N—bis(2-hydroxyethyl)-4-methylaniline | 2.0 |
| Paste B1-4 |  |
| Neopentylglycol dimethacrylate (NPGDMA) | 100 |
| Silane treated $\alpha$-SiO$_2$ | 300 |
| Benzoyl peroxide | 2.0 |
| Paste A1-5 |  |
| Trimethylolpropane triacrylate (TMPT) | 100 |
| Silane treated $\alpha$-SiO$_2$ | 300 |
| N,N—bis(2-hydroxyethyl)-4-methylaniline | 1.5 |

| | Part by weight |
|---|---|
| Paste B1-5 | |
| Trimethylolpropane triacrylate (TMPT) | 100 |
| Silane treated α-SiO₂ | 300 |
| Benzoyl peroxide | 1.5 |

These Paste A's and Paste B's corresponding to sub-numbers were taken each in equal amounts and various composite resins were prepared following the same procedures as the above. Compressive strengths, abrasion loss and bonding strengths were measured of these cured composite resins. Results were shown in Table 1:

| | Part by weight |
|---|---|
| Paste A 2 | |
| DPE-5A ⎫ | |
| DPE-6A ⎭ | 100 in total |
| Silane treated α-SiO₂ | 300 |
| N,N—bis(2-hydroxyethyl)-4-methylaniline | 0.1 |
| Paste B 2 | |
| DPE-5A ⎫ | |
| DPE-6A ⎭ | 100 in total |
| Silane treated α-SiO₂ | 300 |
| Benzoyl peroxide | 1.0 |

TABLE 1

| | Monomer composition tested[*1] | Amount of filler used[*2] (α-SiO₂) | Compressive strength (kg/cm²) | Abrasion loss (cm³) | Bonding strength (kg/cm²) Bovine enamel | Bonding strength (kg/cm²) Bovine dentin |
|---|---|---|---|---|---|---|
| 1 | DPE-5A(55)/DPE-6A(45) | 75 wt. % | 2,520 | 0.47 | 70–80 | 3–10 |
| 2* | Bis-GMA(80)/TEG(20) | " | 2,100 | 0.62 | 40–50 | 0–5 |
| 3* | Bis-MEPP(80)/TEG(20) | " | 2,205 | 0.60 | 30–40 | — |
| 4* | NPGDMA | " | 2,180 | 0.57 | 20–30 | — |
| 5* | TMPT | " | 2,440 | 0.62 | 5–30 | 0 |

(NOTE)
[*1] In the case of mixed monomer, parentheses ( ) following upon a short form for each monomer indicates a weight ratio of the monomer. (The same will apply to the respective tables in the hereinafter-described Examples.)
[*2] The amount of filler used indicates a percentage by weight of the filler based on the total amount of the monomer and the filler. (The same will apply to the respective tables in the hereinafter-described Examples.)
*Indicates Control and the same will apply to the respective tables in the hereinafter-described Examples.

It follows from the above table that the composite resin (Run No. 1) comprising the monomer composition of DPE-5A(55)/DPE-6A(45) belonging to the present invention should be excellent in compressive strength, abrasion loss and bonding strength as compared to the composite resins of Run Nos. 2–5 comprising the monomer compositions of Bis-GMS/TEGDMA, Bis-MEPP/TEGDMA, NPGDMA or TMPT conventionally known as resin-forming monomers for medical or dental use.

EXAMPLE 2

Using, as the monomer, mixed monomers prepared by mixing DPE-5A and DPE-6A in various such proportions as indicated in Table 2, Paste A 2 and Paste B 2 of following compositions were prepared. Paste A 2 and Paste B 2 were mixed and kneaded together following the same procedure as set forth in Example 1 whereby composite resins were prepared.

Compressive strength, abrasion loss, amount of water sorption and bonding to bovine tooth were measured of these cured composite resins. Results were shown in Table 2.

TABLE 2

| | Monomer composition DPE-5A | Monomer composition DPE-6A | Amount of filler used (α-SiO₂) | Compressive strength (kg/cm²) | Abrasion loss (cm³) | Amount of water sorption (mg/cm²) | Bonding strength (kg/cm²) (to bovine dentin) |
|---|---|---|---|---|---|---|---|
| 1 | 100 | 0 | 75 wt. % | 2,430 | 0.46 | 0.35 | 5–10 |
| 2 | 90 | 10 | " | 2,490 | 0.48 | 0.34 | 5–10 |
| 3 | 70 | 30 | " | 2,480 | 0.47 | 0.30 | 4–10 |
| 4 | 50 | 50 | " | 2,510 | 0.47 | 0.38 | 3–10 |
| 5 | 30 | 70 | " | 2,500 | 0.49 | 0.25 | 0–5 |
| 6 | 10 | 90 | " | 2,470 | 0.48 | 0.23 | 0–3 |
| 7 | 0 | 100 | " | 2,480 | 0.53 | 0.20 | 0–2 |

It is noted from the above table that either pentacrylate (DPE-5A) or hexacrylate (DPE-6A) will suffice for the monomer constituting the composite resin of the present invention. The bonding strength value increases in proportion to the increased amount of DPE-5A mixed. For this reason it is conceived that because DPE-5A possesses one more methylol group (—CH₂OH) than the pentacrylate ester, this additional methylol group contributes to the bonding with the hard tissue of the human body.

In the case of the mixed monomer using a combination of DPE-5A and DPE-6A and the mixed monomer prepared by mixing them together in proportions of 30–70 parts by weight of DPE-5A and 70–30 parts by weight of DPE-6A, in particular dental composite resin could be advantageously formed which is excellent in the bonding with the hard tissue of the human body with excellent compressive strength.

In the case, further, of using DPE-5A and DPE-6A in combination, composite resin formed therefrom is found to show excellent water resistance besides the said characteristics.

EXAMPLE 3

Composite resins were prepared following the same procedures of Example 1 except that there were used the mixed monomer of DPE-5A(55)/DPE-6A(45) belonging to the present invention or conventionally known mixed monomer of BisGM(80)/TEG(20) as the resin-forming monomer, given amounts of various inorganic metal oxides conventionally known as the dental inorganic filler listed in Table 3 below as the filler, catalyst and activator in such amounts as set forth in the Table 3. Comparative strength and abrasion loss were measured of these cured composite resins. Results were tabulated in Table 3.

TABLE 3

| Monomer composition | Filler Kind | Filler Amount (wt %) | Amount of activator (part/100 parts of monomer) | Amount of catalyst (part/100 parts of monomer) | Compressive strength (kg/cm$^2$) | Abrasion loss (cm$^3$) |
| --- | --- | --- | --- | --- | --- | --- |
| 1  DPE-5A(55)/DPE-6A(45) | Al$_2$O$_3$ | 75 | 0.8 | 1.0 | 2,530 | 0.49 |
| 2  " | ZrO$_2$ | 70 | 1.0 | 1.5 | 2,400 | 0.46 |
| 3  " | ZrSiO$_4$ | 75 | | | 2,580 | 0.42 |
| 4* Bis-GMA(80)/TEG(20) | Al$_2$O$_3$ | 75 | 0.8 | 1.0 | 2,100 | 0.60 |
| 5* " | ZrO$_2$ | 70 | | | 2,040 | 0.58 |
| 6* " | ZrSiO$_4$ | 75 | | | 2,200 | 0.55 |

*inidcates Control.

It is noted from the above table that if various metal oxides conventionally known as dental inorganic filler are used in combination with conventionally known Bis-GMA type monomers, they will not be fully satisfactory in the point of compressive strength and abrasion resistance, whereas the monomer belonging to the present invention, even if used in combination with these metal oxides, will show fully satisfactory compressive strength and abrasion resistance.

EXAMPLE 4

Using, as the composite resin-forming monomer, DPE-5A(55)/DPE-6A(45) or dipentaerythritol pentamethacrylate (DPE-5M)(55)/dipentaerythritol hexamethacrylate (DPE-6M)(45) Paste A 4-1, B 4-1 and Paste A 4-2 and B 4-2 of following compositions were prepared. Following the same procedure as that of Example 1 these pastes were mixed for the preparation of composite resins.

|  | Part by weight |
| --- | --- |
| Paste A 4-1 | |
| DPE-5A | 55 |
| DPE-6A | 45 |
| Silane treated α-SiO$_2$ | 456 |
| N,N—bis(2-hydroxyethyl)-4-methylaniline | 0.8 |
| Paste B 4-1 | |
| DPE-5A | 55 |
| DPE-6A | 45 |
| Silane treated α-SiO$_2$ | 456 |
| Benzoyl peroxide | 1.0 |
| Paste A 4-2 | |
| Dipentaerythritol pentamethacrylate (DPE-5M) | 55 |
| Dipentaerythritol hexamethacrylate (DPE-6M) | 45 |
| Silane treated α-SiO$_2$ | 456 |
| N,N—bis(2-hydroxyethyl)-4-methylaniline | 0.8 |
| Paste B 4-2 | |
| Dipentaerythritol pentamethacrylate (DPE-5M) | 55 |
| Dipentaerythritol hexamethacrylate (DPE-6M) | 45 |
| Silane treated α-SiO$_2$ | 456 |
| Benzoyl peroxide | 1.0 |

Compressive strength, abrasion loss amount of water sorption were measured of these cured composite resins results were tabulated in Table 4.

TABLE 4

| Monomer composition | Amount of filler used (α-SiO$_2$) | Compressive strength (kg/cm$^2$) | Abrasion loss (cm$^3$) | Amount of water sorption (mg/cm$^2$) |
| --- | --- | --- | --- | --- |
| 1  DPE-5A(55)/DPE-6A(45) | 82 wt. % | 2,750 | 0.35 | 0.28 |
| 2  DPE-5M(55)/DPE-6M(45) | 82 wt. % | 2,800 | 0.38 | 0.25 |

It follows from the above table that if DPE-5M(55)/DPE-6M(45) is to be substituted for DPE-5A(55)/DPE-6A(45) as the composite resin-forming monomer, the dental material obtained will have equally excellent physical properties in the compressive strength, abrasion loss and amount of water sorption. That is, it is noted there that not only dipentaerythritol penta- or hexa-acrylate, but also dipentaerythritol penta- or hexa-methacrylate should be preferred as the composite resin-forming monomer of the present invention.

EXAMPLE 5

Using, as the composite resin-forming monomer, mixed monomers comprising a combination of DPE-5A and DPE-6A belonging to the present invention and conventionally known dental resin-forming monomers Paste A 5-1, B 5-1 and Paste A 5-2 and B 5-2 were prepared. Following the same procedure as that of Example 1 these pastes were mixed for the preparation of composite resins.

|  | Part by weight |
| --- | --- |
| Paste A 5-1 | |
| DPE-5A | 50 |
| DPE-6A | 30 |
| Bis-MEPP | 13 |
| NPGDMA | 7 |
| N,N'—bis(2-hydroxyethyl)-4-dimethylaniline | 1.0 |
| Silane treated α-SiO$_2$ | 456 |
| Paste B 5-1 | |
| DPE-5A | 50 |
| DPE-6A | 30 |
| Bis-MEPP | 13 |
| NPGDMA | 7 |

-continued

| | Part by weight |
|---|---|
| Silane treated α-SiO$_2$ | 456 |
| Benzoyl peroxide | 1.2 |
| Paste A 5-2 | |
| DPE-5A | 50 |
| DPE-6A | 30 |
| Bis-GMA | 10 |
| NPGDMA | 10 |
| N,N—bis(2-hydroxyethyl)-4-methylaniline | 0.8 |
| Silane treated α-SiO$_2$ | 456 |
| Paste B 5-2 | |
| DPE-5A | 50 |
| DPE-6A | 30 |
| Bis-GMA | 10 |
| NPGDMA | 10 |
| Benzoyl peroxide | 1.0 |
| Silane treated Si$_3$N$_4$ | 456 |

Compressive strength and abrasion loss were measured of these cured composite resins and results were tabulated in Table 5.

TABLE 5

| | Monomer composition | Amount of filler used (α-SiO$_2$) | Compressive strength (kg/cm$^2$) | Abrasion loss (cm$^3$) |
|---|---|---|---|---|
| 1 | DPE-5A(50)/DPE-6A(30)/Bis-MEPP(13)/NPG(7) | 82 wt. % | 2,790 | 0.38 |
| 2 | DPE-5A(50)/DPE-6A(30)/Bis-GMA(10)/NPG(10) | 82 wt. % | 2,810 | 0.40 |

It is noticed from the above table that the cured composite resins using mixed monomers prepared by mixing about 20% by weight of conventionally known dental resin-forming monomers, such as Bis-MEPP, NPG, Bis-GMA and so on, to the composite resin-forming monomer belonging to the present invention should also be valuable as dental material in terms of their physical property values. They did not give rise to any compatibility problem.

EXAMPLE 6

Pastes A 6-1, B 6-1, A 6-2, B 6-2, A 6-3, B 6-3, A 6-4 and B 6-4 of the following compositions were prepared using, as the composite resin-forming monomer, mixed monomers prepared by incorporating a given amount of DPE-5A(11)/DPE-6A(9) belonging to the present invention or of conventionally known TEGDMA or NPEDMA into a given amount of conventionally known Bis-GMA or TMPT. Following the same procedure as that of Example 1 these pastes were mixed and kneaded together for the preparation of composite resins.

| | Part by weight |
|---|---|
| Paste A 6-1 | |
| Bisphenol A diglycidyl methacrylate (Bis-GMA) | 80 |
| Dipentaerythritol pentacrylate (DPE-5A) | 11 |
| Dipentaerythritol hexacrylate (DPE-6A) | 9 |
| Silane treated α-SiO$_2$ | 300 |
| N,N—bis(2-hydroxyethyl)-4-methylaniline | 0.8 |
| Paste B 6-1 | |
| Bisphenol A diglycidyl methacrylate (Bis-GMA) | 80 |
| Dipentaerythritol pentacrylate (DPE-5A) | 11 |
| Dipentaerythritol hexacrylate (DPE-6A) | 9 |
| Silane treated α-SiO$_2$ | 300 |
| Benzoyl peroxide | 0.8 |
| Paste A 6-2 | |
| Trimethylolpropane trimethacrylate (TMPT) | 80 |
| Dipentaerythritol pentacrylate (DPE-5A) | 11 |
| Dipentaerythritol hexacrylate (DPE-6A) | 9 |
| Silane treated α-SiO$_2$ | 400 |
| N,N—bis-(2-hydroxyethyl)-4-methylaniline | 1.4 |
| Paste B 6-2 | |
| Trimethylolpropane trimethacrylate (TMPT) | 80 |
| Dipentaerythritol pentacrylate (DPE-5A) | 11 |
| Dipentaerythritol hexacrylate (DPE-6A) | 9 |
| Silane treated α-SiO$_2$ | 400 |
| Benzoyl peroxide | 1.4 |
| Paste A 6-3 | |
| Bisphenol A diglycidyl methacrylate (Bis-GMA) | 80 |
| Triethyleneglycol dimethacrylate (TEGDMA) | 20 |
| Silane treated α-SiO$_2$ | 300 |
| N,N—bis-(2-hydroxyethyl)-4-methylaniline | 0.8 |
| Paste B 6-3 | |
| Bisphenol A diglycidyl methacrylate (Bis-GMA) | 80 |
| Triethyleneglycol dimethacrylate (TEGDMA) | 20 |
| Silane treated α-SiO$_2$ | 300 |
| Benzoyl peroxide | 0.8 |
| Paste A 6-4 | |
| Trimethylolpropane trimethacrylate (TMPT) | 80 |
| Triethyleneglycol dimethacrylate (TEGDMA) | 20 |
| Silane treated α-SiO$_2$ | 400 |
| N,N—bis-(2-hydroxyethyl)-4-methylaniline | 1.5 |
| Paste B 6-4 | |
| Trimethylolpropane trimethylacrylate (TMPT) | 80 |
| Triethyleneglycol dimethacrylate (TEGDMA) | 20 |
| Silane treated α-SiO$_2$ | 400 |
| Benzoyl peroxide | 1.5 |

Compressive strength, abrasion loss and bonding strength to bovine enamel were measured of these cured composite resins. Results were tabulated in Table 6.

TABLE 6

| Monomer composition | Amount of filler used (α-SiO$_2$) | Compressive strength (kg/cm$^2$) | Abrasion loss (cm$^3$) | Bonding strength to bovine enamel (kg/cm$^2$) |
|---|---|---|---|---|
| 1 Bis-GMA(80)/DPE-5A(11)/DPE-6A(9) | 75 wt. % | 2,300 | 0.57 | 50 |
| 2 TMPT(80)/DPE-5M(11)/DPE-6M(9) | 80 wt. % | 2,480 | 0.55 | 25 |
| 3* Bis-GMA(80)/TEGDMA(20) | 75 wt. % | 2,100 | 0.62 | 45 |
| 4* TMPT(80)/NPGDMA(20) | 80 wt. % | 2,400 | 0.60 | 20 |

It is noted from the above table that the composite resins using mixed monomers prepared by mixing the resin-forming monomers belonging to the present invention in the order of 20% by weight as the reactive viscosity controller to the conventionally known dental resin-forming monomers, such as Bis-GMA and TMPT and so on, produce reinforced effects in the aspects of compressive strength, abrasion resistance and bondability to teeth as compared with the composite resins using the same amounts of the conventionally known reactive viscosity controllers, TEGDMA and NPGDMA. Further, the composite resin using the mixed monomer prepared by incorporating NPGDMA of very low viscosity into the low viscosity resin-forming monomer, such as TMPT, is liable to cause the setting of filler and is no good in homogeneity of paste, but in the case of incorporating with the resin-forming monomer of relatively high viscosity belonging to the present invention, the homogeneity of paste is improved.

EXAMPLE 7

Pastes A 7-1, B 7-1, A 7-2, B 7-2, A 7-3, B 7-3, A 7-4, B 7-4, A 7-5 and B 7-5 of the following compositions were prepared using, as the composite resin-forming monomer, mixed monomers prepared by mixing a given amount of DPE-5A(45)/DPE-6A(55) belonging to the present invention to mixture of tetramethylolmethane trimethacrylate (TMM-3M) and tetramethylolmethane tetramethacrylate (TMM-4M) in mix proportions of TMM-3M/TMM-4M=45/55, belonging to the resin-forming monomer in another copending application filed by the instant inventors. Further, 2,5-di-tert-butyl-4-methylphenol (BHT) was incorporated, as a polymerisation inhibitor, into the respective pastes B.

By following the same procedure as that of Example 1 these pastes were mixed and kneaded together for the preparation of composite resins.

|  | Part by weight |
|---|---|
| Paste A 7-1 | |
| Dipentaerythritol pentacrylate (DPE-5A) | 36 |
| Dipentaerythritol hexacrylate (DPE-6A) | 44 |
| Tetramethylolmethane trimethacrylate (TMM-3M) | 9 |
| Tetramethylolmethane tetramethacrylate (TMM-4M) | 11 |
| Silane treated α-SiO₂ | 456 |
| N,N—bis-(2-hydroxyethyl)-4-methylaniline | 2.0 |
| Paste B 7-1 | |
| Dipentaerythritol pentacrylate (DPE-5A) | 36 |
| Dipentaerythritol hexacrylate (DPE-6A) | 44 |
| Tetramethylolmethane trimethacrylate (TMM-3M) | 9 |
| Tetramethylolmethane tetramethacrylate (TMM-4M) | 11 |
| Silane treated α-SiO₂ | 456 |
| Benzoyl peroxide | 2.5 |
| 2,5-di-tert-butyl-4-methylphenyl (BHT) | 0.15 |
| Paste A 7-2 | |
| Dipentaerythritol pentacrylate (DPE-5A) | 22.5 |
| Dipentaerythritol hexacrylate (DPE-6A) | 27.5 |
| Tetramethylolmethane trimethacrylate (TMM-3M) | 22.5 |
| Tetramethylolmethane tetramethacrylate (TMM-4M) | 27.5 |
| Silane treated α-SiO₂ | 456 |
| N,N—bis-(2-hydroxyethyl)-4-methylaniline | 2.0 |
| Paste B 7-2 | |
| Dipentaerythritol pentacrylate (DPE-5A) | 22.5 |
| Dipentaerythritol hexacrylate (DPE-6A) | 27.5 |
| Tetramethylolmethane trimethacrylate (TMM-3M) | 22.5 |
| Tetramethylolmethane tetramethacrylate (TMM-4M) | 27.5 |
| Silane treated α-SiO₂ | 456 |
| Benzoyl peroxide | 2.5 |
| 2,5-di-tert-butyl-4-methylphenol (BHT) | 0.15 |
| Paste A 7-3 | |
| Dipentaerythritol pentacrylate (DPE-5A) | 4.5 |
| Dipentaerythritol hexacrylate (DPE-6A) | 5.5 |
| Tetramethylolmethane trimethacrylate (TMM-3M) | 40.5 |
| Tetramethylolmethane tetramethacrylate (TMM-4M) | 49.5 |
| Silane treated α-SiO₂ | 456 |
| N,N—bis-(2-hydroxyethyl)-4-methylaniline | 2.0 |
| Paste B 7-3 | |
| Dipentaerythritol pentacrylate (DPE-5A) | 4.5 |
| Dipentaerythritol hexacrylate (DPE-6A) | 5.5 |
| Tetramethylolmethane trimethacrylate (TMM-3M) | 40.5 |
| Tetramethylolmethane tetramethacrylate (TMM-4M) | 49.5 |
| Silane treated α-SiO₂ | 456 |
| Benzoyl peroxide | 2.5 |
| 2,5-di-tert-butyl-4-methylphenol (BHT) | 0.15 |
| Paste A 7-4 | |
| Dipentaerythritol pentacrylate (DPE-5A) | 2.25 |
| Dipentaerythritol hexacrylate (DPE-6A) | 2.75 |
| Tetramethylolmethane trimethacrylate (TMM-3M) | 42.75 |
| Tetramethylolmethane tetramethacrylate (TMM-4M) | 52.25 |
| Silane treated α-SiO₂ | 456 |
| N,N—bis-(2-hydroxyethyl)-4-methylaniline | 2.0 |
| Paste B 7-4 | |
| Dipentaerythritol pentacrylate (DPE-5A) | 2.25 |
| Dipentaerythritol hexacrylate (DPE-6A) | 2.75 |
| Tetramethylolmethane trimethacrylate (TMM-3M) | 42.75 |
| Tetramethylolmethane tetramethacrylate (TMM-4M) | 52.25 |
| Silane treated α-SiO₂ | 456 |
| Benzoyl peroxide | 2.5 |
| 2,5-di-tert-butyl-4-methylphenol (BHT) | 0.15 |
| Paste A 7-5 | |
| Tetramethylolmethane trimethacrylate (TMM-3M) | 45 |
| Tetramethylolmethane tetramethacrylate (TMM-4M) | 55 |
| Silane treated α-SiO₂ | 456 |
| N,N—bis-(2-hydroxyethyl)-4-methylaniline | 2.0 |
| Paste B 7-5 | |
| Tetramethylolmethane trimethacrylate (TMM-3M) | 45 |
| Tetramethylolmethane tetramethacrylate (TMM-4M) | 55 |
| Silane treated α-SiO₂ | 456 |
| Benzoyl peroxide | 2.5 |
| 2,5-di-tert-butyl-4-methylphenol (BHT) | 0.15 |

Compressive strength and abrasion loss were measured of these cured composite resins while at the same time, preservation stability tests were attempted for the respective pastes. That is, observations were made of filler setting condition after it was preserved at room temperature for three months. Results were tabulated in Table 7.

TABLE 7

| | Monomer composition | | Amount of filler | Physical properties of cured product | | Paste preservation stability (common to pastes A and B) |
|---|---|---|---|---|---|---|
| No. | DPE-5A(45)/ DPE-6A(55) | TMM-3M(45)/ TMM-4M(55) | used (SiO₂) | Compressive strength (kg/cm²) | Abrasion loss (cm³) | Filler setting condition (after 3 months) |
| 1 | 80 | 20 | 82 | 2,800 | 0.37 | Not observed |
| 2 | 50 | 50 | 82 | 2,790 | 0.38 | Not observed |
| 3 | 40 | 60 | 82 | 2,800 | 0.38 | Not observed |
| 4 | 10 | 90 | 82 | 2,820 | 0.40 | Not observed |
| 5 | 5 | 95 | 82 | 2,810 | 0.39 | Slightly observed |
| 6* | 0 | 100 | 82 | 2,820 | 0.40 | Observed in part |

It is noted from the above table that by incorporating at least 10% by weight of DPE-5A(45)/DPE-6A(55) belonging to the present invention into TMM-3M(45)/TMM-4M(55) belonging to the resin-forming monomer in another copending application, discovered by the instant inventors a long-term preservation stability could be achieved in paste condition without impairing high compressive strength and superior abrasion resistance which are observed in the composite resin using TMM-3M(45)/TMM-4M(55) alone.

EXAMPLE 8

Using, as the composite resin-forming monomer, mixed monomer prepared by mixing DPE-5A and DPE-6A belonging to the present invention in proportions of 55:45 (by weight ratio) and as the powdery filler, conventionally known metal oxide or metal nitride belonging to the present invention in such given amounts as indicated in the following Table 8 Paste A 8 and Paste B 8 of following compositions were prepared.

|  | Part by weight |
|---|---|
| Paste A 8 | |
| Various powdery fillers | in given amounts as indicated in Table 8 |
| DPE-5A(55)/DPE-6A(45) | 100 |
| N,N—bis-(2-hydroxyethyl)-4-methylaniline | 2 |
| Paste B 8 | |
| Various powdery fillers | in given amounts as indicated in Table 8 |
| DPE-5A(55)/DPE-6A(45) | 100 |
| Benzoyl peroxide | 2.5 |
| 2,5-di-tert-butyl-4-methylphenol (BHT) | 0.15 |

Compressive strength and abrasion loss were measured of these cured composite resins. Results were tabulated in Table 8.

TABLE 8

| No. | Monomer composition | Filler Kind | Mohs' hardness | Amount (wt. %) | Compressive strength (kg/cm³) | Abrasion loss (cm³) |
|---|---|---|---|---|---|---|
| 1 | DPE-5A(55)/DPE-6A(45) | $Si_3N_4$ | 9< | 75 | 3,020 | 0.23 |
| 2 | DPE-5A(55)/DPE-6A(45) | $\alpha$-$SiO_2$ | 7 | 75 | 2,520 | 0.47 |
| 3 | DPE-5A(55)/DPE-6A(45) | $Al_2O_3$ | 9 | 75 | 2,570 | 0.49 |
| 4 | DPE-5A(55)/DPE-6A(45) | $Si_3N_4$ | 9< | 80 | 3,400 | 0.18 |
| 5 | DPE-5A(55)/DPE-6A(45) | AlN | 7-8 | 80 | 3,280 | 0.23 |
| 6 | DPE-5A(55)/DPE-6A(45) | ZrN | 8-9 | 80 | 3,210 | 0.25 |
| 7 | DPE-5A(55)/DPE-6A(45) | NbN | 8 | 80 | 3,020 | 0.22 |
| 8 | DPE-5A(55)/DPE-6A(45) | TiN | 8-9 | 80 | 3,250 | 0.28 |
| 9 | DPE-5A(55)/DPE-6A(45) | BN | 9< | 80 | 3,380 | 0.19 |
| 10 | DPE-5A(55)/DPE-6A(45) | VN | 9 | 80 | 3,300 | 0.24 |
| 11 | DPE-5A(55)/$\alpha$-$SiO_2$ |  | 7 | 80 | 2,680 | 0.44 |
| 12 | DPE-6A(45) DPE-5A(55)/ DPE-6A(45) | $Al_2O_3$ | 9 | 80 | 2,720 | 0.45 |

It follows from the above table that when making comparisons of compressive strength and abrasion loss between the cured composite resins (Run Nos. 2, 3, 11 and 12) prepared by combining $\alpha$-$SiO_2$ or $Al_2O_3$, being conventionally known filler, with DPE-5A(55)/DPE-6A(45), being the monomer of the present invention, and the cured composite resins (Run Nos. 1,4–10) in combination with the metal nitride with a Mohs' scale of hardness of 7 or more, the filler of the present invention, the latter ones should be better in the compressive strength and abrasion loss.

It is also noted there that with the cured composite resins using, as the filler, the metal nitride BN, NV and $Si_3N_4$ with a Mohs' scale of hardness of 9 or more show exceptionally high compressive strength and abrasion resistance and that they should be suited to use as crown bridge restoratives or filling materials in molars.

It also follows from comparisons between Run Nos. 1 and 4, between Run Nos. 2 and 11 and between Run Nos. 3 and 12 that the compressive strength and abrasion resistance both are enhanced in proportions to the amount of filler used.

EXAMPLE 9

Composite resins were prepared by using as the composite resin-forming monomer, DPE-5A(55)/DPE-6A(45) belonging to the present invention, conventionally known Bis-GMA(80)/TEGDMA(20) and DPE-5A(44)/DPE-6A(36)/Bis-MEPP(20), as the powdery filler, those fillers mentioned in the following Table 9 in given amounts and further, the activator and the catalyst each in given amounts mentioned in the Table 9. Compressive strength and abrasion loss were measured of these cured composite resins. Results were tabulated in Table 9.

TABLE 9

| No. | Monomer composition | Filler Kind | Amount (wt. %) | Amount of activator (part/200 parts of monomer) | Amount of catalyst (part/200 parts of monomer) | Compressive strength (kg/cm²) | Abrasion loss (cm³) |
|---|---|---|---|---|---|---|---|
| 1 | DPE-5A(55)/DPE-6A(45) | $SiN_4$ | 80 | 2.0 | 2.5 | 3,400 | 0.18 |
| 2 | " | $SiN_4$ | 83 | 2.0 | 2.5 | 3.650 | 0.14 |
| 3 | " | ZrN | 80 | 2.0 | 2.5 | 3,210 | 0.25 |
| 4 | " | TiN | 80 | 2.0 | 2.5 | 3,250 | 0.28 |
| 5 | DPE-5A(44)/DPE-6A(36)/Bis-MEPP(20) | $SiN_4$ | 83 | 1.0 | 2.0 | 3,560 | 0.14 |
| 6* | Bis-GMA(80)/TEG(20) | $\alpha$-$SiO_2$ | 75 | 2.0 | 2.5 | 2,100 | 0.62 |

*BHT was used in the amount of 0.15 (part/200 parts of monomer) in Run Nos. 1–5 and in the amount of 0.25 (part/200 parts of monomer) in Run No. 6.

In the comparisons of the compressive strength as well as the abrasion loss with the cured composite resin (Run No. 6) with a combination of conventionally known monomer Bis-GMA(80)/TEG(20) and known filler $\alpha$-$SiO_2$ a first glance at the above table shows that by making the composite resin-forming material by combining the monomer containing 80% or more of DPE-5A(55)/DPE-6A(45), the monomer of the present invention, with SiN₄, ZrN or TiN, the metal nitride, the composite resin formed should have specifically excellent compressive strength and abrasion resistance.

When comparing the amounts in which the filler can be combined with the composite resin-forming monomer in such a range as not to give rise to the operation problem of the composite resin paste, the monomer containing 80% or more of DPE-5A(55)/DPE-6A(45), the monomer of the present invention, could be incorporated with the filler in greater amounts than the Bis-GMA(80)/TEG(20). This is conceived to be attributed to the difference in the fluid characteristics of the monomer. As is clear from a comparison between Run No. 1 and Run No. 2, because the compressive strength and abrasion resistance increase in proportion to the amount of filler used, obviously the composite resin having a higher compressive strength and abrasion resistance could be obtained when using, as the composite resin-forming material, the monomer of the present invention capable of incorporating a great deal of filler without causing trouble in the operation.

EXAMPLE 10

DPE-5A/DPE-6A, the typical example of the present invention, and conventionally known Big-GMA/-TEGDMA, as the composite resin-forming monomer, and Si₃N₄ and conventionally known α-SiO₂, as the filler were chosen and these monomers and fillers were combined together, considering the operation of composite resin pastes, whereby Paste A 10-1 to A 10-3 and Paste B 10-1 to B 10-3 were prepared.

|  | Part by weight |
|---|---|
| Paste A 10-1 | |
| DPE-5A | 55 |
| DPE-6A | 45 |
| N,N—bis-(2-hydroxyethyl)-4-methylaniline | 2.0 |
| Silane treated Si₃N₄ | 400 |
| Paste B 10-1 | |
| DPE-5A | 55 |
| DPE-6A | 45 |
| Benzoyl peroxide | 2.5 |
| 2,5-di-tert-butyl-4-methylphenol (BHT) | 0.15 |
| Silane treated Si₃N₄ | 400 |
| Paste A 10-2 | |
| DPE-5A | 55 |
| DPE-6A | 45 |
| N,N—bis-(2-hydroxyethyl)-4-methylaniline | 2.0 |
| Silane treated α-SiO₂ | 455 |
| Paste B 10-2 | |
| DPE-5A | 55 |
| DPE-6A | 45 |
| Benzoyl peroxide | 2.5 |
| 2,5-di-tert-butyl-4-methylphenol (BHT) | 0.15 |
| Silane treated α-SiO₂ | 455 |
| Paste A 10-3 | |
| Bis-GMA | 80 |
| TEGDMA | 20 |
| N,N—bis-(2-hydroxyethyl)-4-methylaniline | 2.0 |
| Silane treated α-SiO₂ | 300 |
| Paste B 10-3 | |
| Bis-GMA | 80 |
| TEGDMA | 20 |
| Benzoyl peroxide | 2.5 |
| 2,5-di-tert-butyl-4-methylphenol | 0.15 |
| Silane treated α-SiO₂ | 300 |

Compressive strength, abrasion loss, toothbrush abrasion loss, linear thermal expansion coefficient, Knoop hardness, tensile strength, coloring property and bonding strength were measured of these various cured composite resins. Results were tabulated in Table 10.

TABLE 10

| No. | | | 1 | 2 | 3* |
|---|---|---|---|---|---|
| Monomer composition | | | DPE-5A(55)/ DPE-6A(45) | DPE-5A(55)/ DPE-6A(45) | Bis-GMA(80)/ TEG(20) |
| Filler | Kind | | Si₃N₄ | α-SiO₂ | α-SiO₂ |
|  | Amount (wt. %) | | 80 | 82 | 75 |
| Compressive strength (kg/cm²) | | | 3,400 | 2,750 | 2,100 |
| Abrasion loss (cm³) | | | 0.18 | 0.35 | 0.62 |
| Toothbrush abrasion loss (wt. %) | | | 0.050 | 0.090 | 0.230 |
| Linear thermal expansion coefficient (× 10⁻⁶/°C.) | | | 22.5 | 27.5 | 32.0 |
| Knoop hardness | | | 88 | 74 | 54 |
| Tensile strength (kg/cm²) | | | 500 | 460 | 360 |
| Coloring property (ΔE) | Polished | | 2.52 | 3.40 | 3.88 |
|  | Un-polished | | 4.85 | 8.88 | 10.22 |
| Bonding strength (kg/cm²) | Bovine enamel | (1) | 70–80 | 70–80 | 40–50 |
|  |  | (2) | — | 110–120 | — |
|  | Bovine dentin | | 5–10 | 5–10 | 0–5 |

*indicates Control.

It follows from the above table that the composite resins belonging to the present invention (Run Nos. 1–2), as compared to the composite resin (Run No. 3) prepared by combining together the conventionally known composite resin-forming monomer and filler, have such characteristic features as to be less in the linear thermal expansion coefficient as well as in toothbrush abrasion loss and discoloration or the like, besides markedly excellent mechanical strengths, such as compressive strength, abrasion resistance, Knoop hardness, tensile strength and so on, and markedly excellent bonding to the hard tissue of the human body, and can be advantageously used as medical or dental material. These excellent properties of the composite resins of the present invention are particularly marked in the composite resin (Run No. 1) with a combination of the monomer of the present invention and the filler of the present invention and these composite resins are applicable to molars requiring markedly high mechanical strengths.

In the column of bonding strength to the bovine enamel in the above table, (1) indicates bonding strength when applying the composite resin as such to the bovine enamel and (2) indicates the bonding strength when coating the bovine enamel surface with a mixture of equal amounts of bonding agents A and B of following compositions found anew by the instant inventors and set forth in another copending Patent Application filed claiming the priority based on Japanese Patent Application No. 54-44751, followed by application of the composite resin. It is noted from a comparison of bonding strengths to the bovine enamel in (1) and (2) of Run No. 2 that it is very effective in the point of bondability if the composite resin is applied after precoating the hard tissue of the human body with the said bonding agent.

|  | Part by weight |
|---|---|
| Bonding agent A |  |
| Tetramethylolmethane trimethacrylate | 98 |
| Tetraisopropyltitanate | 2 |
| N,N—bis-(2-hydroxyethyl)-4-methylaniline | 2 |
| Bonding agent B |  |
| Tetramethylolmethane trimethacrylate | 98 |
| Tetraisopropyltitanate | 2 |
| Benzoyl peroxide | 2 |
| 2,5-di-tert-butyl-4-methylphenol | 0.15 |

EXAMPLE 11

Composite resins were prepared by following the same procedure as that of Example 1, using, as the composite resin-forming monomer, DPE-5A(55)/DPE-6A(45) and as the powdered filler, various fillers mentioned hereinafter either alone or in admixture. The following are compositions of the respective pastes used in the preparation of the composite resins.

|  | Part by weight |
|---|---|
| Paste A 11-1 |  |
| Dipentaerythritol pentacrylate (DPE-5A) | 55 |
| Dipentaerythritol hexacrylate (DPE-6A) | 45 |
| Silane treated $Si_3N_4$ | 400 |
| N,N—bis-(2-hydroxyethyl)-4-methylaniline | 2 |
| Paste B 11-1 |  |
| Dipentaerythritol pentacrylate (DPE-5A) | 55 |
| Dipentaerythritol hexacrylate (DPE-6A) | 45 |
| Silane treated $\alpha$-$SiO_2$ | 400 |
| Benzoyl peroxide | 2.5 |
| 2,5-di-tert-butyl-4-methylphenol (BHT) | 0.15 |
| Paste A 11-2 |  |
| Dipentaerythritol pentacrylate (DPE-5A) | 55 |
| Dipentaerythritol hexacrylate (DPE-6A) | 45 |
| Silane treated $Al_2O_3$ | 400 |
| N,N—bis-(2-hydroxyethyl)-4-methylaniline | 2 |
| Paste B 11-2 |  |
| Dipentaerythritol pentacrylate (DPE-5A) | 55 |
| Dipentaerythritol hexacrylate (DPE-6A) | 45 |
| Silane treated $Al_2O_3$ | 400 |
| Benzoyl peroxide | 2.5 |
| 2,5-di-tert-butyl-4-methylphenol (BHT) | 0.15 |
| Paste A 11-3 |  |
| Dipentaerythritol pentacrylate (DPE-5A) | 55 |
| Dipentaerythritol hexacrylate (DPE-6A) | 45 |
| Silane treated $Si_3N_4$ | 400 |
| N,N—bis(2-hydroxyethyl)-4-methylaniline | 2 |
| Paste B 11-3 |  |

|  | Part by weight |
|---|---|
| Dipentaerythritol pentacrylate (DPE-5A) | 80 |
| Dipentaerythritol hexacrylate (DPE-6A) | 20 |
| Silane treated $Si_3N_4$ | 400 |
| Benzoyl peroxide | 2.5 |
| 2,5-di-tert-butyl-4-methylphenol (BHT) | 0.15 |

Compressive strength and abrasion loss were measured of these cured composite resin products, while at the same time, paste stability was observed of the respective pastes under preservation at 40° C. Results were tabulated in Table 11.

TABLE 11

|  | Monomer composition | Filler Kind | Filler A-mount (wt. %) | Compressive strength (kg/cm$^2$) | Abrasion loss (cm$^3$) | B paste stability under preservation at 40° C. |
|---|---|---|---|---|---|---|
| 1 | DPE-5A(55)/ DPE-6A(45) | $Si_3N_4$ $\alpha$-$SiO_2$ | 40 40 | 3,120 | 0.28 | It was not observed to gel even after one month |
| 2 | DPE-5A(55)/ DPE-6A(45) | $Si_3N_4$ $Al_2O_3$ | 40 40 | 3,150 | 0.27 | It was not observed to gel even after one month |
| 3 | DPE-5A(55)/ DPE-6A(45) | $Si_3N_4$ | 80 | 3,400 | 0.18 | It was observed to gel in part after 15 days |

It is noted from the above table that when using the metal nitride in paste A and the known filler $\alpha$-$SiO_2$ or $Al_2O_3$ in paste B in preparing the composite resin by filling the monomer of the present invention with the inorganic filler, as compared with the case of using the metal nitride in both pastes A and B, the composite resin obtained is somewhat inferior in compressive strength or abrasion resistance, but improves in preservability of paste B. That is, this implies that very useful composite resins could be obtained by using the metal nitride in combination with the conventionally known $\alpha$-$SiO_2$ in the monomer of the present invention.

EXAMPLE 12

Paste A 10-1 and Paste B 10-1 and Paste A 10-2 and Paste B 10-2 mentioned in Example 10 were added respectively in equal amounts for the preparation of composite resins of Run Nos. 1 and 2 in the following Table 12. By using them cytotoxicity tests by tissue culture were conducted.

The composite resin was enclosed in a glass tube with a surface area of 28.3 mm$^2$, the specimen immediately after curing was immersed in 5 ml of culture medium (199) and rotated at a rate of 200 r.p.m. at 37° C. for 24 hours and then 1 ml of the medium was interacted with L-cells (3.4 × 10$^4$) to count cell numbers after 2 days and after 4 days. Results were shown in Table 12.

Likewise, cytotoxity tests were conducted on the composite resin comprising Paste A 1-2 and Paste B 1-2 of Example 1 and results were also tabulated in Table 12.

TABLE 12

| | Monomer composition | Filler Kind | Filler Amount (wt %) | Cell number in 1 ml After 2 days | Cell number in 1 ml After 4 days |
|---|---|---|---|---|---|
| Blank | — | — | — | 5.6 × 10⁴ | 68 × 10⁴ |
| 1 | DPE-5A(55)/DPE-6A(45) | Si₃N₄ | 80 | 4.2 × 10⁴ | 32 × 10⁴ |
| 2 | DPE-5A(55)/DPE-6A(45) | α-SiO₂ | 80 | 4.3 × 10⁴ | 30 × 10⁴ |
| 3* | Bis-GMA(80)/TEGDMA(20) | α-SiO₂ | 75 | 3.4 × 10⁴ | 22 × 10⁴ |

*indicates Control.

It is noted from the above table that the cell multiplication inhibitory action shown by both the composite resins (Run No. 1 and Run No. 2 in Table 12) of the present invention is equivalent to, or even less than, that of the Bis-GMA type composite resin (Run No. 3 in Table 12, identified as Run No. 2 in Table 1) which is regarded as relatively low in tissue irritation as compared with the spot cure type resins.

EXAMPLE 13

Measurement of surface uncured percent:

Surface uncured percent was measured by following procedures.

About 0.58 g each of paste A and paste B were taken and kneaded together for 30 seconds. Then the mixture was raised and weighed (B) in the portion about 1 cm from the end of a kneading bar which was weighed in advance (A).

Five (5) minutes after the beginning of kneading uncured layer on the surface of cured product was strongly wiped off by gauze for 30 seconds and then it was once again weighed (C). Uncured percent on the surface of cured product=uncured amount/specimen amount was figured out by the following equation:

$$\text{Surface uncured percent (\%)} = \frac{C - B}{B - A} \times 100$$

Further, this measurement was conducted under environment of 22±0.5° C.

Using, as the monomer, monomers obtained by mixing in various proportions as indicated in Table 13 below a mixed monomer of DPE-5A(55)/DPE-6A(45) belonging to the present invention and a mixed monomer of TMM-3A(60)/TMM-4A(40) belonging to the subject matter of Japanese Patent Application No. 55-41084, U.S. patent application No. 138,814 and European Patent application No. 80101964.7, separately discovered by the instant inventors, paste A 13 and paste B 13 were mixed in the same manner as in Example 1 whereby composite resins were prepared.

| | Part by weight |
|---|---|
| Paste A 13 | |
| DPE-5A(55)/DPE-6A(45) ⎫ | |
| TMM-3A(60)/TMM-4A(40) ⎭ | 100 in total |
| Silane treated α-SiO₂ | 400 |
| N,N—bis-(2-hydroxyethyl)-4-methylaniline | 1.0 |
| Paste B 13 | |
| DPE-5A(55)/DPE-6A(45) ⎫ | |
| TMM-3A(60)/TMM-4A(40) ⎭ | 100 in total |
| Silane treated α-SiO₂ | 400 |

| | Part by weight |
|---|---|
| Benzoyl peroxide | 1.0 |

Surface uncured percent after the curing of these composite resins was measured. Results were shown in Table 13.

TABLE 13

| No. | Monomer composition DPE-5A(55)/DPE-6A(45) | TMM-3A(60)/TMM-4A(40) | Surface uncured percent(%) |
|---|---|---|---|
| 1 | 100 | 0 | 0.8 |
| 2 | 80 | 20 | 0.8 |
| 3 | 60 | 40 | 1.0 |
| 4 | 40 | 60 | 1.2 |
| 5 | 20 | 80 | 1.2 |
| 6 | 0 | 100 | 1.5 |

It is noted from the above table that the composite resin prepared by using, as the monomer, the mixed type monomer of DPE-5A(55)/DPE-6A(45) belonging to the present invention is superior in surface curability of cured product to the composite resin prepared by using, as the monomer, the mixed type monomer of TMM-3A(60)/TMM-4A(40) and that even on the occasion of using the mixed type monomer of DPE-5A(55)/DPE-6A(45) and TMM-3A(60)/TMM-4A(40), the surface curability of the cured composite resin is improved as mixed ratio of DPE-5A(55)/DPE-6A(55) is increased.

What we claim are:

1. A dental restorative composition comprising (I) 30 to 95% by weight of finely divided, inorganic filler which is effective for use in a dental restorative material, has a Mohs' hardness of at least 5 and has a particle diameter of from 0.01 to 50 microns and (II) 5 to 70% by weight of a resin-forming material for dental use, said resin-forming material comprising a blend of (1) 30 to 95% by weight of at least one monomer having the formula (II):

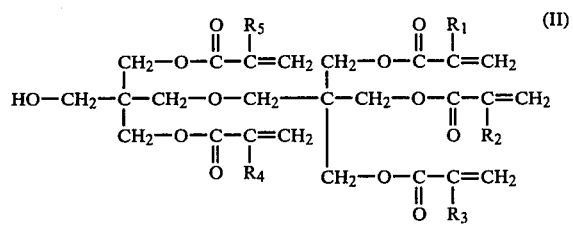

wherein R₁, R₂, R₃, R₄ and R₅ represent hydrogen or methyl, and (2) 70 to 5% by weight of at least one monomer having the formula (III):

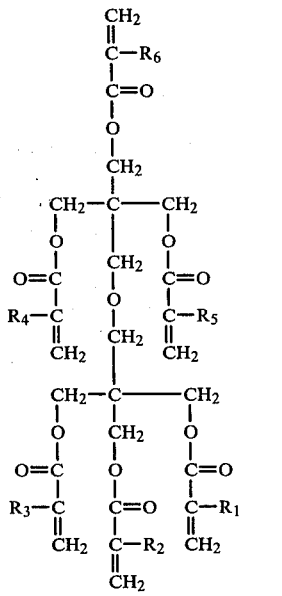

(III)

wherein $R_1$, $R_2$, $R_3$, $R_4$ and $R_5$ have the same meanings as defined in the formula (II), and $R_6$ represents hydrogen or methyl.

2. A composition according to claim 1, in which said resin-forming material consists essentially of a blend of
   (1) 40 to 80% by weight of at least one compound having the formula (II) and
   (2) 60 to 20% by weight of at least one compound having the formula (III).

3. A composition according to claim 1, in which said resin-forming material consists essentially of a blend of 40 to 80% by weight of dipentaerythritol pentacrylate and 60 to 20% by weight of dipentaerythritol hexacrylate.

4. A dental restorative composition comprising
   (I) 30 to 95% by weight of finely divided, inorganic filler which is effective for use in a dental restorative material, has a Mohs' hardness of at least 5 and has a particle diameter of from 0.01 to 50 microns
   and
   (II) 5 to 70% by weight of a resin-forming material for dental use, said resin-forming material comprising
      (A) 40 to 10% by weight of a blend of monomers comprising
         (1) 30 to 95% by weight of at least one compound having the formula (II):

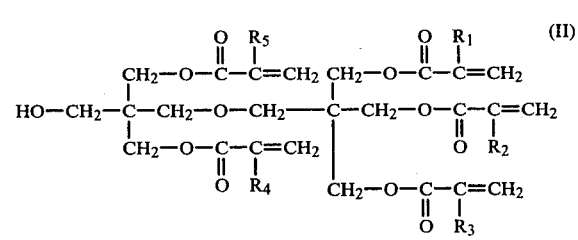

(II)

wherein $R_1$, $R_2$, $R_3$, $R_4$ and $R_5$ represent hydrogen or methyl,
and (2) 70 to 5% by weight of at least one compound having the formula (III):

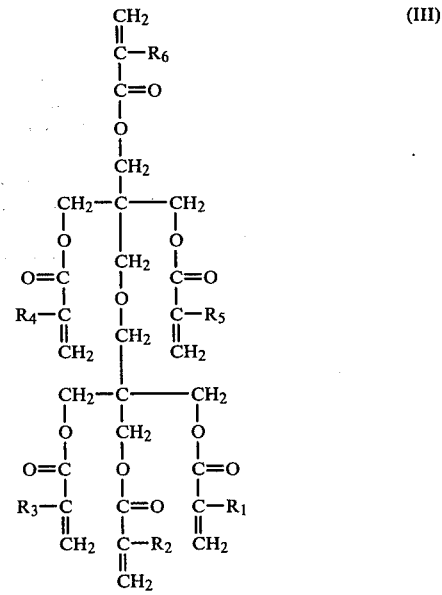

(III)

wherein $R_1$, $R_2$, $R_3$, $R_4$ and $R_5$ have the same meanings as defined in the formula (II), and $R_6$ represents hydrogen or methyl,
and
      (B) 60 to 90% by weight of at least one compound having the formula (IV):

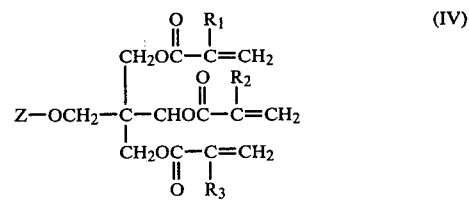

(IV)

wherein Z is hydrogen or

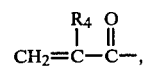

and $R_1$, $R_2$, $R_3$ and $R_4$, which are the same or different, have the same meanings as defined in the formula (II).

5. A composition according to claim 4, in which component A of said resin-forming material consists essentially of
   (1) 45 to 70% by weight of at least one compound having the formula (II) and
   (2) 55 to 30% by weight of at least one compound having the formula (III).

6. A composition according to claim 4, in which the formula II compound is dipentaerythritol pentacrylate and the formula III compound is dipentaerythritol hexacrylate.

7. A composition of matter consisting essentially of a set of two pastes adapted to be mixed together so as to be cured, one of said pastes consisting essentially of a composition as claimed in claim 1 mixed with a peroxide catalyst effective for polymerizing and curing said composition, the other of said pastes consisting essentially of a composition as claimed in claim 29 mixed with an activator for activating the polymerization, the amount of said catalyst being from 0.1 to 2.5% by weight, based on the weights of said compounds of formulas (II) and (III), and the amount of said activator being from 0.1 to 2.5% by weight, based on the weights of said compounds of formulas (II) and (III).

8. A composition of matter as claimed in claim 7, in which said catalyst is selected from the group consisting of diacyl peroxides, hydroperoxides, ketone peroxides and peroxycarbonates, and said activator is selected from the group consisting of tertiary amines, transition metal ions and amine salts of p-toluene sulphonic acid and sulphinic acid.

9. A composition of matter consisting essentially of a set of two pastes adapted to be mixed together so as to be cured, one of said pastes consisting essentially of a composition as claimed in claim 4, mixed with a peroxide catalyst effective for polymerizing and curing said composition, the other of said pastes consisting essentially of a composition as claimed in claim 4 mixed with an activator for activating the polymerization, the amount of said catalyst being from 0.1 to 2.5% by weight, based on the weights of said compounds of formulas (II) and (III), and the amount of said activator being from 0.1 to 2.5% by weight, based on the weights of said compounds of formulas (II) and (III).

10. A composition of matter as claimed in claim 9, in which said catalyst is selected from the group consisting of diacyl peroxides, hydroperoxides, ketone peroxides and peroxycarbonates, and said activator is selected from the group consisting of tertiary amines, transition metal ions and amine salts of p-toluene sulphonic acid and sulphinic acid.

* * * * *